United States Patent
Cherpeck

[11] Patent Number: 6,114,542
[45] Date of Patent: Sep. 5, 2000

[54] ETHERS OF POLYALKYL OR POLYALKENYL N-HYDROXYALKYL SUCCINIMIDES AND FUEL COMPOSITIONS CONTAINING THE SAME

[75] Inventor: Richard E. Cherpeck, Cotati, Calif.

[73] Assignee: Chevron Chemical Company LLC, San Francisco, Calif.

[21] Appl. No.: 09/141,633

[22] Filed: Aug. 28, 1998

[51] Int. Cl.$^7$ .......................... C07D 207/40; C10L 1/22; C07C 9/22
[52] U.S. Cl. ................. 548/547; 44/347; 585/18
[58] Field of Search ............... 548/547; 44/347; 585/18

[56] References Cited

U.S. PATENT DOCUMENTS

| | | | |
|---|---|---|---|
| 3,394,144 | 7/1968 | Giles et al. | 260/326 |
| 4,919,684 | 4/1990 | Nalesnik et al. | 44/62 |
| 5,393,309 | 2/1995 | Cherpeck | 44/347 |
| 5,620,486 | 4/1997 | Cherpeck | 44/347 |

FOREIGN PATENT DOCUMENTS 0 241 417  4/1967  Russian Federation .

*Primary Examiner*—Joseph McKane
*Assistant Examiner*—Dominic Keating
*Attorney, Agent, or Firm*—Claude J. Caroli

[57] ABSTRACT

Ethers of polyalkyl or polyalkenyl N-hydroxyalkyl succinimides having the formula:

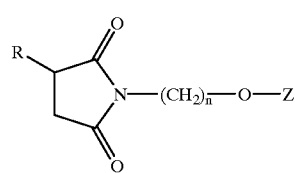

(I)

or a fuel soluble salt thereof.

The compounds of formula I are useful as fuel additives for the prevention and control of engine deposits.

42 Claims, No Drawings

ETHERS OF POLYALKYL OR POLYALKENYL N-HYDROXYALKYL SUCCINIMIDES AND FUEL COMPOSITIONS CONTAINING THE SAME

BACKGROUND OF THE INVENTION

1. Field of the Invention

This invention relates to ethers of polyalkyl or polyalkenyl N-hydroxyalkyl succinimides and derivatives thereof. In a further aspect, this invention relates to the use of these compounds in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted succinimides are known to reduce engine deposits when used in fuel compositions. U.S. Pat. No. 5,393,309, issued Feb. 28, 1995 to R. E. Cherpeck, discloses a fuel additive composition comprising (a) a polyisobutenyl succinimide derived from ethylenediamine or diethylenetriamine, wherein the polyisobutenyl group has an average molecular weight of about 1200 to 1500 and (b) a nonvolatile paraffinic or naphthenic carrier oil, or a mixture thereof.

Similarly, U.S. Pat. No. 5,620,486, issued Apr. 15, 1997 to R. E. Cherpeck, discloses fuel compositions containing hydrocarbyl-substituted N-aryl succinimides wherein the nitrogen atom on the succinimide is substituted with a phenyl ring having one or two substituents selected from hydroxy, carboxyl, nitro, amino and alkylamino.

N-Hydroxyalkyl succinimides are also known in the art. For example, U.S. Pat. No. 3,394,144, issued Jul. 23, 1968 to Giles et al., discloses N-2-hydroxyethyl succinimide and N-3-hydroxypropyl succinimide, which are useful as intermediates in the preparation of substituted anthraquinone dyes for hydrophobic textile materials.

In addition, U.S.S.R. Patent No. 241,417, published Apr. 18, 1969, discloses beta-succinimidoethyl esters of aryloxyalkanecarboxylic acids, which are prepared by reacting beta-succinimidoethanol with aryloxyalkylcarboxylic acids.

SUMMARY OF THE INVENTION

I have now discovered certain ethers of polyalkyl or polyalkenyl N-hydroxyalkyl succinimides which provide excellent control of engine deposits, especially intake valve deposits, when employed as fuel additives in fuel compositions.

The compounds of the present invention include those having the following formula and fuel soluble salts thereof:

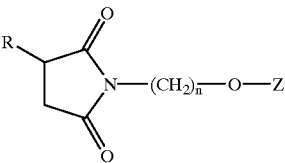

(I)

wherein
  R is a polyalkyl or polyalkenyl group having an average molecular weight in the range of about 450 to about 5,000;
  n is an integer from 2 to 5; and
  Z is a moiety selected from the group consising of

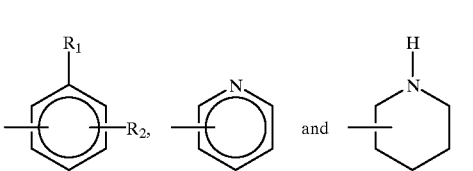

(I)

wherein
  $R_1$ is hydroxy, nitro, cyano or —$(CH_2)_x$—$NR_3R_4$, wherein $R_3$ and $R_4$ are independently hydrogen or lower alkyl of 1 to 6 carbon atoms and x is 0 or 1; and
  $R_2$ is hydrogen, hydroxy, nitro, cyano or —$(CH_2)_y$—$NR_5R_6$, wherein $R_5$ and $R_6$ are independently hydrogen or lower alkyl of 1 to 6 carbon atoms and y is 0 or 1.

The present invention further provides a fuel composition comprising a major amount of hydrocarbons boiling in the gasoline or diesel range and a deposit-controlling effective amount of a compound of the present invention.

The present invention additionally provides a fuel concentrate comprising an inert stable oleophilic organic solvent boiling in the range of from about 150° F. to 400° F. and from about 10 to 70 weight percent of a compound of the present invention.

Among other factors, the present invention is based on the surprising discovery that certain ethers of polyalkyl or polyalkenyl N-hydroxyalkyl succinimides provide excellent control of engine deposits, especially on intake valves, when employed as additives in fuel compositions.

DETAILED DESCRIPTION OF THE INVENTION

Based on performance (e.g. deposit control), handling properties and performance/cost effectiveness, preferred compounds of the invention are those wherein Z is substituted phenyl, wherein $R_1$ is nitro, amino, N-alkylamino, or —$CH_2NH_2$ (aminomethyl). More preferably, $R_1$ is a nitro, amino or —$CH_2NH_2$ group. Most preferably, $R_1$ is an amino or —$CH_2NH_2$ group, especially amino. Preferably, $R_2$ is hydrogen, hydroxy, nitro or amino. More preferably, $R_2$ is hydrogen or hydroxy. Most preferably, $R_2$ is hydrogen. Preferably, R is a polyalkyl or polyalkenyl group having an average molecular weight in the range of about 500 to 3,000, more preferably about 700 to 3,000, and most preferably about 900 to 2,500. Preferably, the compound has a combination of preferred substituents.

Preferably, n is an integer of from 2 to 3.

When $R_1$ and/or $R_2$ is an N-alkylamino group, the alkyl group of the N-alkylamino moiety preferably contains 1 to 4 carbon atoms. More preferably, the N-alkylamino is N-methylamino or N-ethylamino.

Similarly, when $R_1$ and/or $R_2$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

A further preferred group of compounds are those wherein Z is substituted phenyl, wherein $R_1$ is amino, nitro, or —$CH_2NH_2$ and $R_2$ is hydrogen or hydroxy. A particularly preferred group of compounds are those wherein $R_1$ is amino, $R_2$ is hydrogen, R is a polyalkyl or polyalkenyl group derived from polyisobutene, and n is 2 or 3.

Another preferred group of compounds are those wherein Z is pyridyl or piperidyl, R is a polyalkyl or polyalkenyl group derived from polyisobutene, and n is 2 or 3.

It is preferred that the $R_1$ substituent is located at the meta or, more preferably, the para position of the phenoxy moiety, i.e., para or meta relative to the ether oxygen. When $R_2$ is a substituent other than hydrogen, it is particularly preferred that this $R_2$ group be in a meta or para position relative to the ether oxygen and in an ortho position relative to the $R_1$ substituent. Further, in general, when $R_2$ is other than hydrogen, it is preferred that one of $R_1$ or $R_2$ is located para to the ether oxygen and the other is located meta to the ether oxygen.

Similarly, when Z is pyridyl or piperidyl, it is preferred that the nitrogen atom in the pyridyl or piperidyl ring is located para or meta, more preferably para, relative to the ether oxygen.

The compounds of the present invention will generally have a sufficient molecular weight so as to be non-volatile at normal engine intake valve operating temperatures (about 200°–250° C.). Typically, the molecular weight of the compounds of this invention will range from about 700 to about 3,500, preferably from about 700 to about 2,500.

Fuel-soluble salts of the compounds of formula I can be readily prepared for those compounds containing an amino or substituted amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

When the $R_1$ or $R_2$ substituent is a hydroxy group, suitable salts can be obtained by deprotonation of the hydroxy group with a base. Such salts include salts of alkali metals, alkaline earth metals, ammonium and substituted ammonium salts. Preferred salts of hydroxy-substituted compounds include alkali metal, alkaline earth metal and substituted ammonium salts.

Definitions

As used herein, the following terms have the following meanings unless expressly stated to the contrary.

The term "amino" refers to the group: —$NH_2$.

The term "N-alkylamino" refers to the group: —$NHR_a$ wherein $R_a$ is an alkyl group. The term "N,N-dialkylamino" refers to the group: —$NR_bR_c$, wherein $R_b$ and $R_c$ are alkyl groups.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "polyalkyl" or "polyalkenyl" refers to an alkyl or alkenyl group, respectively, which is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The term "fuel" or "hydrocarbon fuel" refers to normally liquid hydrocarbons having boiling points in the range of gasoline and diesel fuels.

General Synthetic Procedures

The ethers of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, N.Y., 1991, and references cited therein.

In the present synthetic procedures, a hydroxyl group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the aromatic ethers of this invention having an amino group on the aromatic moiety will generally be prepared from the corresponding nitro derivative. accordingly, in many of the following procedures, a nitro group will serve as a protecting group for the amino moiety.

Moreover, the compounds of this invention having a —$CH_2NH_2$ group on the aromatic moiety will generally be prepared from the corresponding cyano derivative, —CN. Thus, in many of the following procedures, a cyano group will serve as a protecting group for the —$CH_2NH_2$ moiety.

Synthesis

The esters of the present invention may be prepared by a process which initially involves reaction of a polyalkyl or polyalkenyl succinic anhydride of the formula:

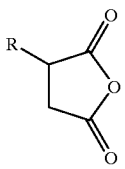

(II)

wherein R is as defined herein, with an alkanolamine of the formula:

(III)

wherein n is defined herein, to provide a polyalkyl or polyalkenyl N-hydroxyalkyl succinimide of the formula:

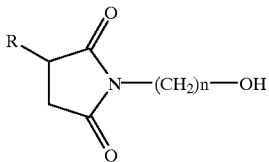

(IV)

wherein R and n are as defined herein.

The polyalkyl or polyalkenyl succinic anhydrides of Formula II are typically prepared by the reaction of maleic anhydride with the desired polyolefin or chlorinated polyolefin, under reaction conditions well known in the art. For example, such succinic anhydrides may be prepared by the thermal reaction of a polyolefin and maleic anhydride, as described, for example, in U.S. Pat. Nos. 3,361,673 and 3,676,089. Alternatively, the substituted succinic anhydrides can be prepared by the reaction of chlorinated polyolefins with maleic anhydride, as described, for example, in U.S. Pat. No. 3,172,892. A further discussion of hydrocarbyl-substituted succinic anhydrides can be found, for example, in U.S. Pat. Nos. 5,620,486 and 5,393,309.

Polyalkenyl succinic anhydrides may be converted to polyalkyl succinic anhydrides by using conventional reducing conditions such as catalytic hydrogenation. For catalytic hydrogenation, a preferred catalyst is palladium on carbon. Likewise, polyalkenyl succinimides may be converted to polyalkyl succinimides using similar reducing conditions.

The polyalkyl or polyalkenyl substituent on the succinic anhydrides employed in the invention is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

A particularly preferred polyalkyl or polyalkenyl substituent is one derived from polyisobutene.

The preferred polyisobutenes used to prepare the presently employed polyalkyl or polyalkenyl succinic anhydrides are polyisobutenes which comprise at least about 20% of the more reactive methylvinylidene isomer, preferably at least 50% and more preferably at least 70%. Suitable polyisobutenes include those prepared using BF$_3$ catalysts. The preparation of such polyisobutenes in which the methylvinylidene isomer comprises a high percentage of the total composition is described in U.S. Pat. Nos. 4,152,499 and 4,605,808. Examples of suitable polyisobutenes having a high alkylvinylidene content include Ultravis 30, a polyisobutene having a number average molecular weight of about 1300 and a methylvinylidene content of about 74%, and Ultravis 10, a polyisobutene having a number average molecular weight of about 950 and a methylvinylidene content of about 76%, both available from British Petroleum.

The alkanolamines of Formula III are known compounds which are available commercially or can be readily prepared using conventional procedures. Suitable alkanolamines include 2-aminoethanol, 3-amino-1-propanol, 4-amino-1-butanol, and 5-amino-1-pentanol. Preferred alkanolamines are 2-aminoethanol and 3-amino-1-propanol.

The polyalkyl or polyalkenyl succinic anhydride and alkanolamine are generally reacted in essentially equivalent amounts at a temperature in the range of about 100° C. to 200° C., and preferably from about 125° C. to about 175° C. The reaction may take place in the presence or absence of an inert solvent.

The time of reaction will vary depending on the particular succinic anhydride and alkanolamine reactants, and the reaction temperature. Generally, the reaction time will range from about one hour to about 24 hours. At the completion of the reaction, the polyalkyl or polyalkenyl N-hydroxyalkyl succinimide product is isolated using conventional techniques.

The reaction of succinic anhydrides with alkanolamines is known in the art and is described, for example, in U.S. Pat. No. 3,394,144.

The polyalkyl or polyalkenyl N-hydroxyalkyl succinimide of formula IV is then deprotonated with a suitable base to provide the metal salt of the N-hydroxyalkyl succinimide, which is subsequently reacted with a substituted phenyl halide of formula VI or a pyridyl halide of formula VII to provide the aromatic ether compounds of formula I. The aromatic halide compounds of formulas VI and VII can be represented as follows:

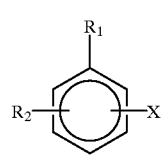

(VI)

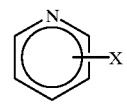

(VII)

wherein R$_1$ and R$_2$ are as defined herein, and X is a halogen, such as fluoro, chloro, or bromo, and wherein any hydroxy or amino substituent on the substituted phenyl halide of formula VI is preferably protected with a suitable protecting group, for example, a benzyl or nitro group, respectively. Moreover, a —CH$_2$NH$_2$ substituent on the aromatic ring will preferably be protected by the use of a cyano group, CN.

Generally, the deprotonation reaction will be effected by contacting the polyalkyl or polyalkenyl N-hydroxyalkyl succinimide of formula IV with a strong base, such as sodium hydride, potassium hydride, sodium amide, potassium hydroxide, and the like, in an inert solvent, such as toluene, xylene, and the like, under substantially anhydrous conditions at a temperature in the range of about −10° C. to about 120° C. for about 0.25 to about 3 hours. This reaction may also be promoted by copper salts. See, for example, J. Lindley, *Tetrahedron*, Vol. 40, pp. 1433–1456, 1984.

The metal salt of the N-hydroxyalkyl succinimide is generally not isolated, but is reacted in situ with about 0.8 to about 2.0 molar equivalents of the substituted and suitably protected phenyl halide of formula VI or pyridyl halide of formula VII. Typically, this reaction is conducted in a substantially anhydrous inert solvent at a temperature in the range of about 30° C. to about 160° C. for about 0.5 to about 48 hours. Suitable solvents for this reaction include toluene, xylene, tetrahydrofuran, and the like. The reaction will generally be conducted at a pressure sufficient to contain the reactants and the solvent, preferably at atmospheric or ambient pressure.

The substituted phenyl halides of formula VI are generally known compounds and can be prepared from known compounds using conventional procedures or obvious modifications thereof. Representative phenyl halides which may be used as starting materials and, if necessary, when suitably protected, include, for example, 4-fluoronitrobenzene, 4-bromonitrobenzene, 3-fluoronitrobenzene, 3-bromonitrobenzene, 2-hydroxy-4-fluoronitrobenzene, 2-hydroxy-4-bromonitrobenzene, 2-nitro-4-fluorophenol, and 2-nitro-4-bromophenol. When the $R_1$ substituent is —$CH_2$—$NR_3R_4$, suitable starting materials include, for example, 4-fluorocyanobenzene, 4-bromocyanobenzene, 3-fluorocyanobenzene, and 3-bromocyanobenzene.

Preferred substituted phenyl halides include 4-fluoronitrobenzene, 2-hydroxy-4-fluoronitrobenzene, and 4-fluorocyanobenzene.

The pyridyl halides of formula VII are also known compounds and include 4-fluoropyridine and 3-fluoropyridine.

When the substituted phenyl halides of formula VI contain a hydroxyl group, protection of the aromatic hydroxyl groups may be accomplished using well-known procedures. The choice of a suitable protecting group for a particular hydroxy-substituted phenyl halide will be apparent to those skilled in the art. Various protecting groups, and their introduction and removal, are described, for example, in T. W. Greene and P. G. M. Wuts, *Protective Groups in Organic Synthesis,* Second Edition, Wiley, N.Y., 1991, and references cited therein.

After completion of the etherification reaction, deprotection of the aromatic hydroxyl group can also be accomplished using conventional procedures. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

When the substituted phenyl halides of formula VI have a free amino group (—$NH_2$) on the phenyl moiety, it is generally desirable to employ the corresponding nitro compound (i.e., where $R_1$ and/or $R_2$ is a nitro group) and then reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron and the like, in the presence of an acid, such as dilute hydrochloric acid. Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate and the like. Hydrogenation of aromatic nitro groups is discussed in further detail in, for example, P. N. Rylander, *Catalytic Hydrogenation in Organic Synthesis,* pp. 113–137, Academic Press (1979); and *Organic Synthesis, Collective Vol.* 1, Second Edition, pp. 240–241, John Wiley & Sons, Inc. (1941); and references cited therein.

Likewise, when the substituted phenyl halides of formula VI contain a —$CH_2NH_2$ group on the phenyl moiety, it is generally desirable to employ the corresponding cyano compounds (i.e., where $R_1$ and/or $R_2$ is a —CN group), and then reduce the cyano group to a —$CH_2NH_2$ group using conventional procedures. Aromatic cyano groups may be reduced to —$CH_2NH_2$ groups using procedures well known in the art. For example, aromatic cyano groups may be reduced under catalytic hydrogenation conditions similar to those described above for reduction of aromatic nitro groups to amino groups. Thus, this reaction is typically conducted using about 1 to 4 atmospheres of hydrogen and a platinum or palladium catalyst, such as palladium on carbon. Another suitable catalyst is a Lindlar catalyst, which is palladium on calcium carbonate. The hydrogenation may be carried out at temperatures of about 0° C. to about 100° C. for about 1 to 24 hours in an inert solvent such as ethanol, ethyl acetate, and the like. Hydrogenation of aromatic cyano groups is further discussed in the references cited above for reduction of aromatic nitro groups.

In a similar fashion, compounds of formula I wherein the substituent Z is a piperidyl group may be conveniently prepared by first preparing the corresponding pyridyl compound (i.e., where Z is pyridyl), and then reducing the pyridyl group to a piperidyl group using conventional reducing conditions. Hydrogenation of pyridyl groups is discussed in further detail in, for example, P. N. Rylander, *Catalytic Hydrogenation in Organic Synthesis,* pp. 213–220, Academic Press (1979); and in M. Hudlicky, *Reductions in Organic Chemistry,* Second Edition, pp. 69–71, ACS monograph: 188, American Chemical Society (1996); and references cited therein.

An alternative procedure for preparing the compounds of formula I involves initially deprotonating an alkanolamine of formula III with a suitable base, such as sodium hydride, to form the metal salt of the alkanolamine, and then reacting the metal salt with a substituted phenyl halide of formula VI or a pyridyl halide of formula VII, under reaction conditions as described above, to provide a phenyl or pyridyl ether of the alkanolamine of formula III. The phenyl or pyridyl ether of the alkanolamine is then reacted with a polyalkyl or polyalkenyl succinic anhydride of formula II to provide the succinimides of formula I, using the above reaction conditions for forming succinimides from the anhydride.

Fuel Compositions

The compounds of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the compounds of this invention in hydrocarbon fuel will range from about 50 to about 2500 parts per million (ppm) by weight, preferably from 75 to 1,000 ppm. When other deposit control additives are present, a lesser amount of the present additive may be used.

The compounds of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, hydrocarbyl poly(oxyalkylene) aminocarbamates, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the ethers of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 to Robinson and 5,004,478 to Vogel et al., and in European Application Nos. 356,726, published Mar. 7, 1990, and 382,159, published Aug. 16, 1990.

These carrier fluids are believed to act as a carrier for the fuel additives of the present invention and to assist in removing and retarding deposits. The carrier fluid may also exhibit synergistic deposit control properties when used in combination with an ether compound of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

PREPARATIONS AND EXAMPLES

A further understanding of the invention can be had in the following nonlimiting Examples. Wherein unless expressly stated to the contrary, all temperatures and temperature ranges refer to the Centigrade system and the term "ambient" or "room temperature" refers to about 20° C.–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dt), quartets (q), and multiplets (m), and cps refers to cycles per second.

Example 1

Preparation of

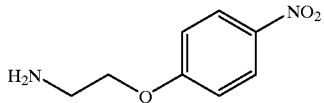

To a flask equipped with a magnetic stirrer, reflux condensor, thermocouple, septa and nitrogen inlet was added sodium hydride (4.7 grams, 60 weight percent dispersion in mineral oil) and anhydrous methyl sulfoxide (50 mL). The contents of the flask were heated to 40° C. for 30 minutes. The solution was cooled to room temperature and ethanolamine (6.2 mL) was added. 1-Fluoro-4-nitrobenzene (10.0 mL) was added dropwise so that the temperature was approximately 30° C. did not exceed 40° C. The reaction was stirred for 30 minutes, then diluted with dichloromethane (150 mL) and washed with water (3×100 mL). The organic layer was dried over anhydrous magnesium sulfate, filtered and concentrated in vacuo to yield 8.4 grams of the desired product as an orange oil.

Example 2

Preparation of

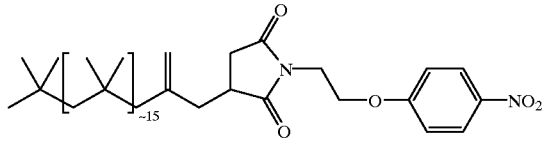

To a flask equipped with a mechanical stirrer, Dean-Stark trap, thermometer, reflux condensor and nitrogen inlet was added 31.2 grams of polyisobutenylsuccinic anhydride (0.03 moles, saponification number=77.6, derived from polyisobutene which had an approximate molecular weight of 950 and a methylvinylidene content of 86%). The product from Example 1 (5.5 grams, 0.03 moles) was added and the mixture was stirred at room temperature for 30 minutes, 50° C. for 30 minutes and 175° C. for 36 hours to yield a viscous oil after cooling to room temperature. The resultant oil were chromatographed on silica gel eluting with hexane/ethyl acetate (7:1), followed by hexane/ethyl acetate (3.2) and ethyl acetate to yield 25.9 grams of the desired succinimide.

Example 3

Preparation of

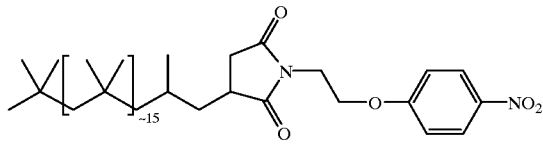

A solution of 15.5 grams of the product from Example 2 in 150 mL of ethyl acetate and 100 mL of toluene containing 2.3 grams of 10% palladium on charcoal was hydrogenated at 50 psi for 72 hours on a Parr low-pressure hydrogenator. Catalyst filtration and removal of the solvent in vacuo yielded 11.3 grams of the desired aniline as an oil. $^1$H NMR (CDCl$_3$) δ 6.75 (AB quartet, 2H), 6.6 (AB quartet, 2H), 4.05 (t, 2H), 3.9 (t, 2H), 3.5 (bs, 2H), 0.7–3.1 (m, 140H).

Example 4

Preparation of

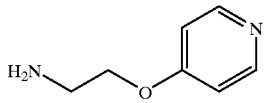

To a flask equipped with a magnetic stirrer, reflux condenser, thermocouple, septa and nitrogen inlet was added sodium hydride (4.7 grams, 60 weight percent dispersion in mineral oil). Ethanolamine (11.2 mL) was added and the contents of the flask were stirred at room temperature for 30 minutes. 4-Chloropyridine hydrochloride (13.9 grams dissolved in 109 mL of ethanolamine) was added dropwise and the reaction was stirred at 100° C. for sixteen hours. The reaction was diluted with toluene (400 mL), filtered and concentrated in vacuo to yield the desired product.

Example 5

Preparation of

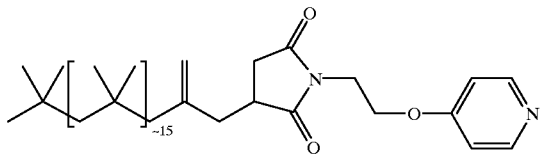

To a flask equipped with a mechanical stirrer, Dean-Stark trap, thermometer, reflux condensor and nitrogen inlet was added 23.0 grams of polyisobutenylsuccinic anhydride (0.03 moles, saponification number=77.6, derived from polyisobutene which had an approximate molecular weight of 950 and a methylvinylidene content of 86%). The product from Example 4 (4.6 grams, 0.03 moles) was added and the mixture was stirred at 170° C. for 16 hours to yield a viscous oil after cooling to room temperature. The resultant oil was diluted with hexane (300 mL) and washed with water (3×100 mL) followed by saturated aqeous sodium chloride (1×100 mL). The organic layer was dried over anhydrous magnesium sulfate, filtered and concentrated in vacuo to yield the desired succinimide.

Example 6

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

| Sample[1] | Intake Valve Deposit Weight (in milligrams) | | |
|---|---|---|---|
| | Run 1 | Run 2 | Average |
| Base Fuel | 365.2 | 343.1 | 354.2 |
| Example 3 | 195.0 | — | 195.0 |

[1]At 50 parts per million actives (ppma) and 50 ppm of α-hydroxy-ω-4-dodecylphenoxypoly(oxypropylene) having an average of 12–13 oxypropylene units (prepared essentially as described in Example 6 of U.S. Pat. No. 4,160,648) carrier oil.

The base fuel employed in the above single-cylinder engine tests was a regular octane unleaded gasoline containing no fuel detergent. The test compounds were admixed with the base fuel to give a concentration of 50 ppma (parts per million actives) and 50 ppm of α-hydroxy-ω-4-dodecylphenoxypoly(oxypropylene) having an average of 12–13 oxypropylene units (prepared essentially as described in Example 6 of U.S. Pat. No. 4,160,648) carrier oil.

The data in Table I illustrates the significant reduction in intake valve deposits provided by an ether of the present invention (Examples 3) compared to the base fuel, even at a very low additive concentration.

What is claimed is:

1. A compound of the formula:

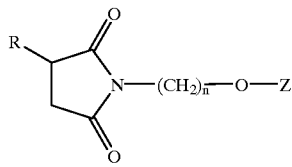

or a fuel soluble salt thereof; wherein

R is a polyalkyl or polyalkenyl group having an average molecular weight in the range of about 500 to 3,000;

n is an integer from 2 to 5; and Z is

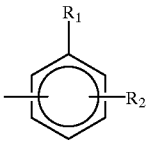

wherein $R_1$ is a nitro, cyano or —$(CH_2)_x$—$NR_3R_4$, wherein $R_3$ and $R_4$ are independently hydrogen or lower alkyl of 1 to 6 carbon atoms and x is 0 or 1; and $R_2$ is hydrogen, nitro, cyano or —$(CH_2)_y$—$NR_5R_6$, wherein $R_5$ and $R_6$ are independently hydrogen or lower alkyl of 1 to 6 carbon atoms and y is 0 or 1.

2. The compound according to claim 1, wherein $R_1$ is nitro, amino or —$CH_2NH_2$.

3. The compound according to claim 2, wherein $R_1$ is amino, or —$CH_2NH_2$.

4. The compound according to claim 3, wherein $R_1$ is amino.

5. The compound according to claim 1, wherein $R_2$ is hydrogen, nitro or amino.

6. The compound according to claim 5, wherein $R_2$ is hydrogen.

7. The compound according to claim 1, wherein R is a polyalkyl or polyalkenyl group having an average molecular weight in the range of about 700 to 3,000.

8. The compound according to claim 7, wherein R is a polyalkyl or polyalkenyl group having an average molecular weight in the range of about 900 to 2,500.

9. The compound according to claim 1, wherein R is a polyalkyl or polyalkenyl group derived from polypropylene, polybutene, or a polyalphaolefin oligomer of 1-octene or 1-decene.

10. The compound according to claim 9, wherein R is a polyalkyl or polyalkenyl group derived from polyisobutene.

11. The compound according to claim 10, wherein the polyisobutene contains at least about 20% of a methylvinylidene isomer.

12. The compound according to claim 1, wherein n is 2 or 3.

13. The compound according to claim 1, wherein Z is substituted phenyl wherein $R_1$ is amino and $R_2$ is hydrogen, R is a polyalkyl or polyalkenyl group derived from polyisobutene, and n is 2 or 3.

14. A fuel composition comprising a major amount of hydrocarbons boiling in the gasoline or diesel range and an effective deposit-controlling amount of a compound of the formula:

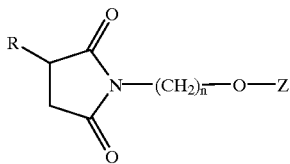

or a fuel soluble salt thereof; wherein

R is a polyalkyl or polyalkenyl group having an average molecular weight in the range of about 500 to 3,000;

n is an integer from 2 to 5; and Z is

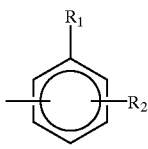

wherein $R_1$ is nitro, cyano or $-(CH_2)_x-NR_3R_4$, wherein $R_3$ and $R_4$ are independently hydrogen or lower alkyl of 1 to 6 carbon atoms and x is 0 or 1; and $R_2$ is hydrogen, nitro, cyano or $-(CH_2)_y-NR_5R_6$, wherein $R_5$ and $R_6$ are independently hydrogen or lower alkyl of 1 to 6 carbon atoms and y is 0 or 1.

15. The fuel composition according to claim 14, wherein $R_1$ is nitro, amino or $-CH_2NH_2$.

16. The fuel composition according to claim 15, wherein $R_1$ is amino, or $-CH_2NH_2$.

17. The fuel composition according to claim 16, wherein $R_1$ is amino.

18. The fuel composition according to claim 14, wherein $R_2$ is hydrogen, nitro or amino.

19. The fuel composition according to claim 18, wherein $R_2$ is hydrogen.

20. The fuel composition according to claim 14, wherein R is a polyalkyl or polyalkenyl group having an average molecular weight in the range of about 700 to 3,000.

21. The fuel composition according to claim 20, wherein R is a polyalkyl or polyalkenyl-group having an average molecular weight in the range of about 900 to 2,500.

22. The fuel composition according to claim 14, wherein R is a polyalkyl or polyalkenyl group derived from polypropylene, polybutene, or a polyalphaolefin oligomer of 1-octene or 1-decene.

23. The fuel composition according to claim 22, wherein R is a polyalkyl or polyalkenyl group derived from polyisobutene.

24. The fuel composition according to claim 23, wherein the polyisobutene contains at least about 20% of a methylvinylidene isomer.

25. The fuel composition according to claim 14, wherein n is 2 or 3.

26. The fuel composition according to claim 14, wherein Z is substituted phenyl wherein $R_1$ is amino and $R_2$ is hydrogen, R is a polyalkyl or polyalkenyl group derived from polyisobutene, and n is 2 or 3.

27. The fuel composition according to claim 14, wherein the composition contains from about 50 to about 2,000 parts per million by weight of said compound.

28. The fuel composition according to claim 14, where the composition further contains from about 100 to about 5,000 parts per million by weight of a fuel-soluble, nonvolatile carrier fluid.

29. A fuel concentrate comprising an inert stable oleophilic organic solvent boiling in the range of from about 150° F. to 400° F. and from about 10 to about 70 weight percent of a compound of the formula:

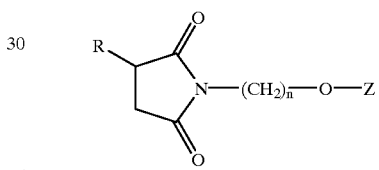

or a fuel soluble salt thereof; wherein

R is a polyalkyl or polyalkenyl group having an average molecular weight in the range of about 500 to 3,000;

n is an integer from 2 to 5; and Z is

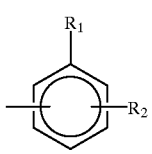

wherein $R_1$ is nitro, cyano or $-(CH_2)_x-NR_3R_4$, wherein $R_3$ and $R_4$ are independently hydrogen or lower alkyl of 1 to 6 carbon atoms and x is 0 or 1; and $R_2$ is hydrogen, nitro, cyano or $-(CH_2)_y-NR_5R_6$, wherein $R_5$ and $R_6$ are independently hydrogen or lower alkyl of 1 to 6 carbon atoms and y is 0 or 1.

30. The fuel concentrate according to claim 29, wherein $R_1$ is nitro, amino or $-CH_2NH_2$.

31. The fuel concentrate according to claim 30, wherein $R_1$ is amino, or $-CH_2NH_2$.

32. The fuel concentrate according to claim 31, wherein $R_1$ is amino.

33. The fuel concentrate according to claim 29, wherein $R_2$ is hydrogen, nitro or amino.

34. The fuel concentrate according to claim 29, wherein $R_2$ is hydrogen.

35. The fuel concentrate according to claim 29, wherein R is a polyalkyl or polyalkenyl group having an average molecular weight in the range of about 700 to 3,000.

36. The fuel concentrate according to claim 35, wherein R is a polyalkyl or polyalkenyl group having an average molecular weight in the range of about 900 to 2,500.

37. The fuel concentrate according to claim 29, wherein R is a polyalkyl or polyalkenyl group derived from polypropylene, polybutene, or a polyalphaolefin oligomer of 1-octene or 1-decene.

38. The fuel concentrate according to claim 37, wherein R is a polyalkyl or polyalkenyl group derived from polyisobutene.

39. The fuel concentrate according to claim 38, wherein the polyisobutene contains at least about 20% of a methylvinylidene isomer.

40. The fuel concentrate according to claim 29, wherein n is 2 or 3.

41. The fuel concentrate according to claim 29, wherein Z is substituted phenyl wherein $R_1$ is amino and $R_2$ is hydrogen, R is a polyalkyl or polyalkenyl group derived from polyisobutene, and n is 2 or 3.

42. The fuel concentrate according to claim 29, wherein the fuel concentrate further contains from about 20 to about 60 weight percent of a fuel-soluble, nonvolatile carrier fluid.

\* \* \* \* \*